United States Patent [19]

Buescher, Jr. et al.

[11] Patent Number: 5,598,738
[45] Date of Patent: Feb. 4, 1997

[54] LOAD APPARATUS AND METHOD FOR BOLT-LOADED COMPACT TENSION TEST SPECIMEN

[75] Inventors: Brent J. Buescher, Jr.; W. Randolph Lloyd; Michael B. Ward; Jonathan S. Epstein, all of Idaho Falls, Id.

[73] Assignee: Lockheed Idaho Technologies Company, Idaho Falls, Id.

[21] Appl. No.: 415,879

[22] Filed: Apr. 3, 1995

[51] Int. Cl.$^6$ ............................................. F16B 31/02
[52] U.S. Cl. .............................................. 73/761; 73/768
[58] Field of Search ........................... 73/761, 768, 774, 73/799, 826, 856

[56] References Cited

U.S. PATENT DOCUMENTS

| | | | |
|---|---|---|---|
| 2,747,454 | 5/1956 | Bowersett | 73/761 |
| 3,943,819 | 3/1976 | Charron | 73/761 |
| 3,983,745 | 10/1976 | Juusola | 73/799 |
| 4,090,489 | 5/1978 | Barker | 73/799 |
| 4,429,579 | 2/1984 | Wilhelm | 73/768 |
| 4,481,826 | 11/1984 | Ingraffea | 73/799 |
| 5,291,789 | 3/1994 | Walton | 73/761 |

OTHER PUBLICATIONS

"Load Bolts for Static Tension, Compression, or Bending Loads", *Omega Complete Pressure, Strain and Force Measurement Handbook and Encyclopedia*, Omega Engineering, vol. 27 (Upated).

Gilbreath, W. P., et al., "Aqueous Stress–Corrosion Cracking of High–Toughness D6AC Steel", *Gilbreath and Adamson on Aqueous Cracking*, pp. 176–188., 1976.

Moore, P. G., et al., "Automated Monitoring of Stress Corrosion Crack Growth Rates in Laboratory Specimens", *Proceedings/Computer Aided Acquisition and Analysis of Corrosion Data*, vol. 85–3 (1984).

Novak, S. R., et al., "Modified WOL Specimen for $K_{Iscc}$ Environmental Testing", Symposium on Stress Corrosion and corrosion Principles, *Journal of Materials*, ASTM Fall Meeting, pp. 701–724 (1968).

Primary Examiner—Richard Chilcot
Assistant Examiner—Max Noori
Attorney, Agent, or Firm—Wells St. John Roberts Gregory & Matkin

[57] ABSTRACT

A bolt-loaded compact tension test specimen load apparatus includes: a) a body having first and second opposing longitudinal ends, the first end comprising an externally threaded portion sized to be threadedly received within the test specimen threaded opening; b) a longitudinal loading rod having first and second opposing longitudinal ends, the loading rod being slidably received in a longitudinal direction within the body internally through the externally threaded portion and slidably extending longitudinally outward of the body first longitudinal end; c) a force sensitive transducer slidably received within the body and positioned to engage relative to the loading rod second longitudinal end; and d) a loading bolt threadedly received relative to the body, the loading bolt having a bearing end surface and being positioned to bear against the transducer to forcibly sandwich the transducer between the loading bolt and loading rod. Also disclosed is a method of in situ determining applied force during crack propagation in a bolt-loaded compact tension test specimen.

19 Claims, 3 Drawing Sheets

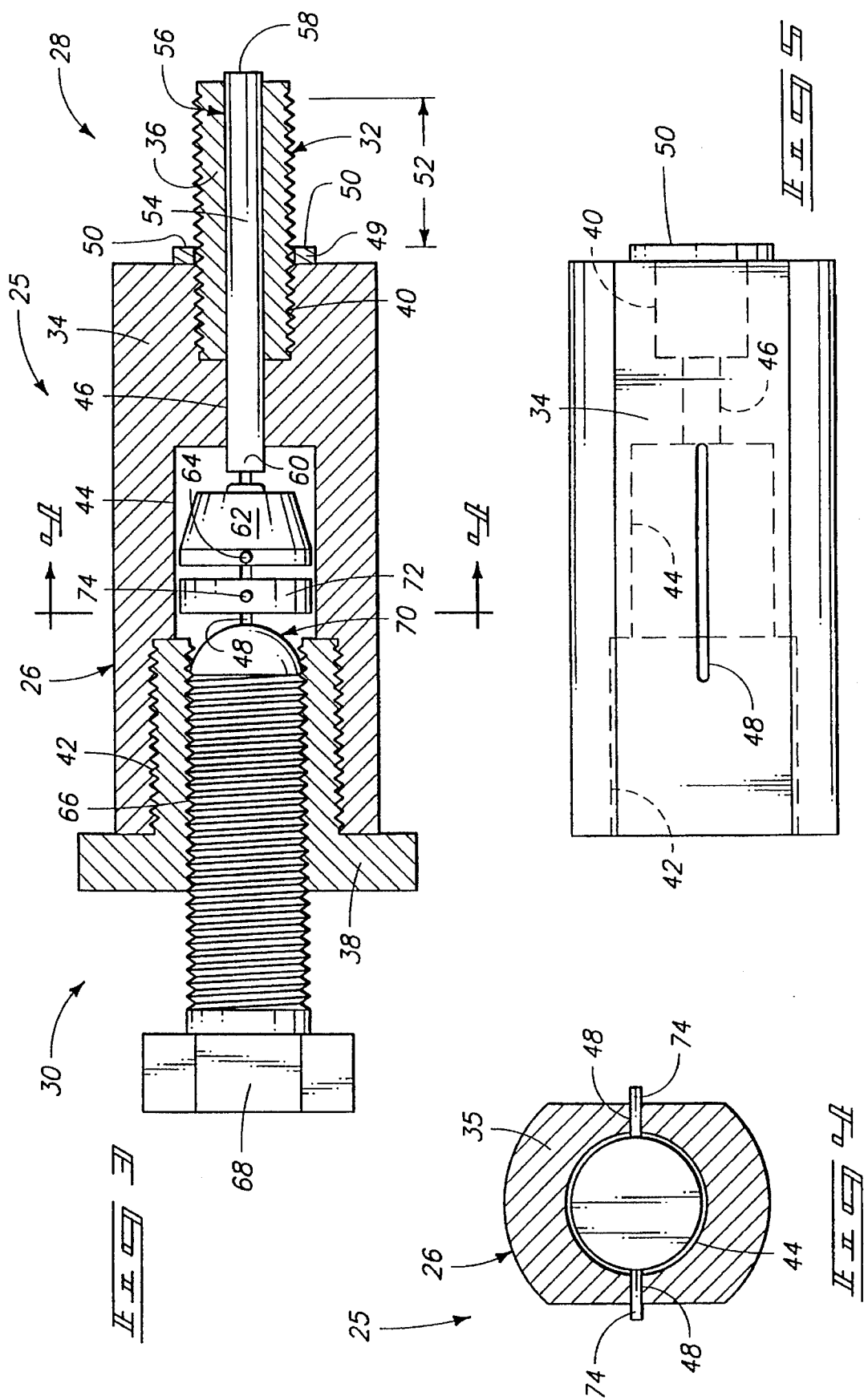

5,598,738

LOAD APPARATUS AND METHOD FOR BOLT-LOADED COMPACT TENSION TEST SPECIMEN

CONTRACTUAL ORIGIN OF THE INVENTION

The United States Government has rights in this invention disclosed under contract number DE-AC07-76ID01570 between the U.S. Department of Energy and EG&G Idaho, Inc., now contract number DE-AC07-94ID13223 with Lockheed Idaho Technologies Company.

TECHNICAL FIELD

This invention relates to methods and apparatus for in situ determination of load during crack propagation analysis in bolt-loaded compact tension [C(T)] test specimens.

BACKGROUND OF THE INVENTION

A major concern in the use of high strength metallic materials is the rapid growth of small flaws and defects as a result of the combined effects of tensile stresses and environment, something commonly referred to as stress-corrosion cracking. The resistance of material to such cracking can be quantified by fracture mechanics analysis. Fracture mechanics allows determination of the combined effects of stress and crack size in terms of a parameter K, the stress intensity factor. It has been shown that there exists a threshold value of K, called $K_{iscc}$. This threshold value is determined for static loading conditions, and is considered to be an intrinsic material property which is utilized in structural design to compute allowable flaw size. Crack propagation rates as a function of applied stress intensity are used in combination with estimated or determined maximum initial flaw size to set inspection intervals for marine and other structures.

There are two generally accepted methods for determining $K_{iscc}$, referred to as K-increasing and K-decreasing methods. With the increasing method, pre-cracked, cantilever-loaded beam specimens are maintained under constant applied load in the environment of interest for a fixed period of time that is specific to the material. Because K will increase rapidly with increasing crack length in the cantilever specimen, once crack growth begins it proceeds quickly to failure. Bracketing methods, involving specimens which fail and specimens where no stress-corrosion cracking is observed, are used to determine $K_{iscc}$ to about 10% precision. Little or no information concerning crack growth rates are obtained from cantilever bend tests.

A bolt-loaded compact tension [C(T)] test specimen is used for K-decreasing test methods. Such is generally described with reference to FIG. 1. The typical test involves fabricating a test specimen 10 from the material of interest into the shape shown in FIG. 1, and to certain specific dimensions. A typical test specimen constitutes a block of material having overall length, height and width dimensions of 3.2 inches, 2.48 inches and 1.0 inch, respectively. Alternate sized specimens can of course be utilized. A notch 12 is provided into specimen 10 from one end thereof. A threaded opening 14 extends from the top of specimen 10 downwardly to and transversely relative to notch 12. Notch 12 has an open spacing 15, and threaded opening 14 has a length 11 from the top exterior of the specimen to the notch. For purposes which will be apparent from the continuing discussion, this spacing and length in combination have a sum defining a first distance 19.

A hole 16 is provided through the thickness of specimen 10 in a precisely located manner to intersect through notch 12 as shown. A hardened steel tip 18 is separately provided and slidable within hole 16. It has an upper flat surface 20 which is coincident with the base of notch 12. Tip 18 is made of a material which is harder than the material of specimen 10. A threaded loading bolt 22 is received within threaded opening 14 for loading the specimen. Bolt 22 is threaded inwardly until its inner flat end bears against tip surface 20, upon which the specimen begins to experience load. The value of K can be computed from the measured value of the crack mouth opening before and after load, with such being recorded by an electronic crack mouth opening displacement gauge. Typically at this point, the specimen is inserted into the aggressive environment. This will typically lower the fracture energy of the material causing a crack 33 to grow under fixed displacement provided by loading bolt 22 against the tip.

Because the crack opening displacement is constant during this type of test, both load and K decrease as the crack extends. A specimen is loaded to a high value of K so that crack growth begins quickly and continues until K decreases to $K_{isoc}$, when crack growth arrests. Once crack growth can no longer be observed, the test is effectively finished. Crack length and standard fracture-mechanics equations are then utilized to computer $K_{iscc}$.

Unfortunately, the typical industry standard methods for determining final load include unloading and reloading the specimen at the end of the test. This incurs time, and hence money, and even then only one load data point at or near the end of the test is attained. It would be much more cost-effective to simply be able to record the arrest load or the entire load history during crack growth in situ during test.

Many different schemes have evolved for estimating bolt-induced specimen load in situ. One technique is to provide a strain gauge on the end surface of the specimen opposite the inner crack tip, such as at location 31. The strain during test is correlated with the estimated applied bolt-load through a secondary calculation performed in an approximating manner. This analytic method, commonly referred to as specimen compliance, breaks down when more than one crack initiates from the initial specimen crack, or substantial crack front curvature occurs.

Another method involves placing a strain gauge upon the load tup. Again, some form of calibration must be performed between the measured tup strain and applied load to the tup. Even this calibration is not accurate due to complex three-dimensional stress fields provided on the tup from Hertzian contact between the rotating bolt and non-rotating tup. Further, this Hertzian contact is impacted by any frictional unloading hysteresis effects that occur during the crack growth process as the energy in the specimen is transferred into growing the crack.

Yet another method uses an instrumented bolt having an internal hollow portion and strain gauge provided therein. Calibration must be conducted to account for the above-described Hertzian contact stresses.

It would be desirable to improve upon prior art methods and devices for determining crack propagation and load in bolt-loaded compact tension test specimens.

BRIEF DESCRIPTION OF THE DRAWINGS

Preferred embodiments of the invention are described below with reference to the following accompanying drawings.

FIG. 3 is a diagrammatic side elevational cross-section view of a bolt-loaded compact tension test specimen load apparatus in accordance with the invention.

FIG. 4 is a sectional view taken through line 4—4 of FIG. 3.

FIG. 5 is a diagrammatic side elevational view of a component shown in FIG. 3.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with one aspect of the invention, a bolt-loaded compact tension test specimen load apparatus comprises:

a body having first and second opposing longitudinal ends, the first end comprising an externally threaded portion sized to be threadedly received within the test specimen threaded opening;

a longitudinal loading rod having first and second opposing longitudinal ends, the loading rod being slidably received in a longitudinal direction within the body internally through the externally threaded portion and slidably extending longitudinally outward of the body first longitudinal end;

a force sensitive transducer slidably received within the body and positioned to engage relative to the loading rod second longitudinal end; and a loading bolt threadedly received relative to the body, the loading bolt having a bearing end surface and being positioned to bear against the transducer to forcibly sandwich the transducer between the loading bolt and loading rod.

In accordance with another aspect of the invention, a method of in situ determining applied force during crack propagation in a bolt-loaded compact tension test specimen comprises the following steps:

providing a rod in a transversely slidable orientation relative to a notch in a bolt-loaded compact tension test specimen, the rod having first and second opposing ends, the first end being positioned and adapted for bearing against one transverse surface of the test specimen exposed by the notch;

providing a force sensitive transducer operatively against the second end of the loading rod;

threading a bolt operatively against the transducer to force the first rod end against the one transverse surface of the test specimen to load the test specimen; and determining applied force on the test specimen as a function of time from readings obtained from the force sensitive transducer.

Figure 1:
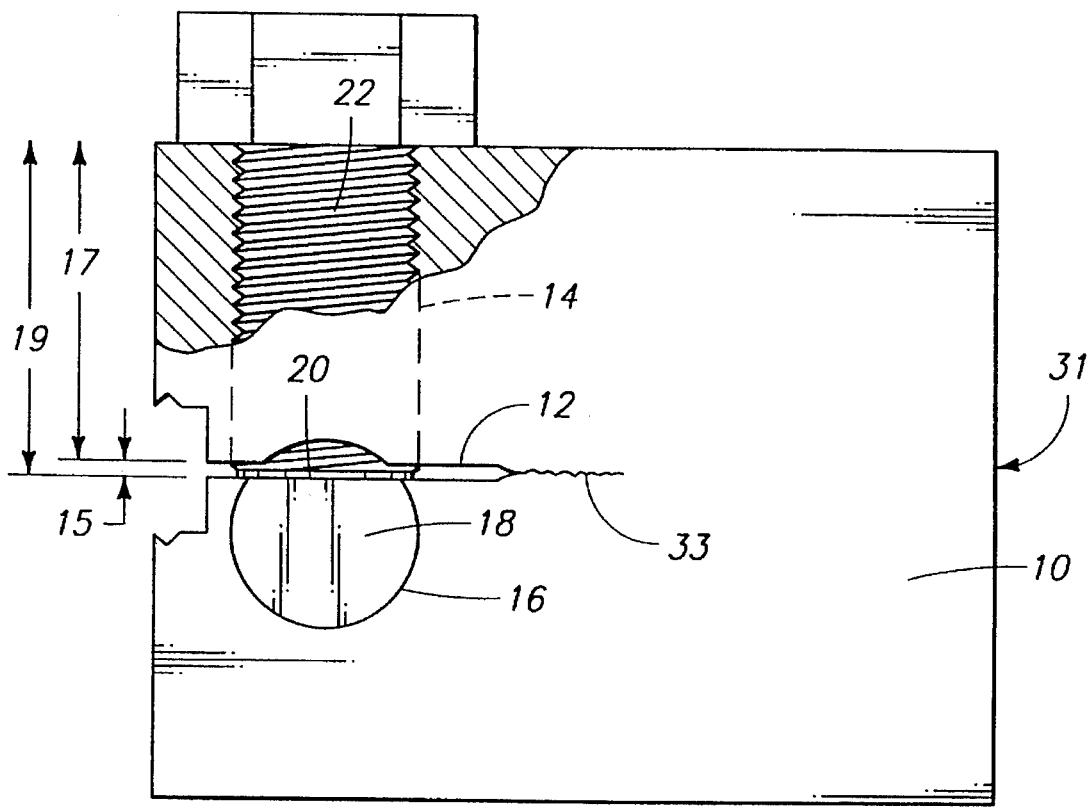
FIG. 1 is a side elevational view of a bolt-loaded compact tension test specimen for which this invention was principally designed, and is discussed in the "Background" section above.
Figure 2:
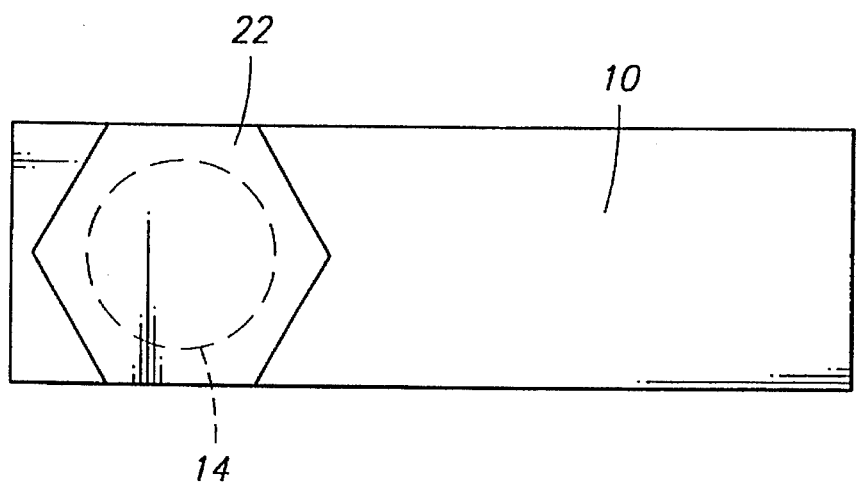
FIG. 2 is a top view of FIG. 1.
Figure 6:
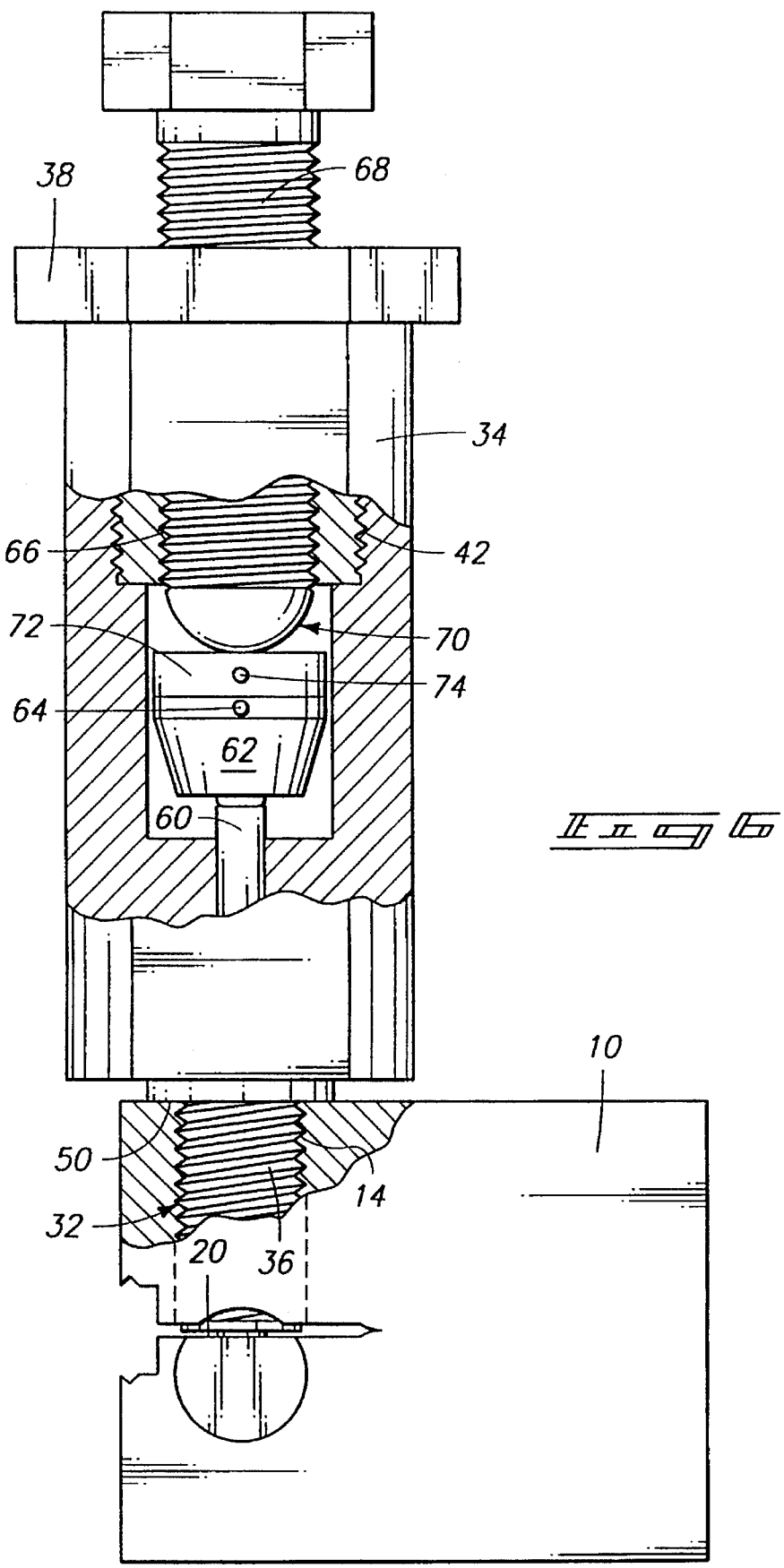
FIG. 6 is an assembled view of the FIG. 3 load apparatus associated with a bolt-loaded compact tension test specimen of FIG. 1.

More particularly and with reference to FIGS. 3–6, a load apparatus for a bolt-loaded compact tension test specimen is indicated generally with reference numeral 25. Load apparatus 25 comprises a body 26 having first and second opposing longitudinal ends 28 and 30, respectively. First end 28 comprises an externally threaded portion 32 sized to be threadedly received within test specimen threaded opening 14 (FIGS. 1, 2 and 6). More particularly, body 26 is comprised of three discrete major components, namely a main body portion 34, a fore longitudinally elongated specimen adapter body 36, and an aft plug 38.

Main body 34 has a first longitudinal threaded opening 40 at its first end. A second longitudinal threaded opening 42 is provided at the second end of main body 34. A pair of central longitudinal cavities 44 and 46 interconnect threaded openings 42 and 40, such that a continuous longitudinal cavity is provided through main body 34. Cavity 46 is narrower in lateral cross-section than opening 44. A pair of side longitudinal slots 48 are also provided in main body 34.

Specimen adapter body 36 has external threads which are both sized to be threadedly received within threaded opening 40 of main body 34 and test specimen threaded opening 14. Main body 34 includes a projecting annular ring 49 formed about threaded opening 40 at end 28, and defines a bearing surface 50. With discrete body 36 fully received within main body portion 34, adapter body 36 longitudinally extends from main body bearing surface 50 outwardly to a second distance 52. Second distance 52 is effectively less than combination first distance 19 of notch 12 and threaded opening 14 (FIG. 1). This enables easy reference positioning of main body bearing surface 50 relative to the exterior of test specimen 10 when discrete body 36 is fully threaded inwardly relative to test specimen threaded opening 14 (FIG. 6).

A longitudinal loading rod 54 is slidably received in a longitudinal direction within body 26 internally through externally threaded portion 32 and slidably extends longitudinally outward of body first longitudinal end 28. More particularly, externally threaded longitudinal extension 36 is provided with a central, longitudinal internal bore 56 through which loading rod 54 is slidably received. Main body longitudinal cavity 46 aligns with bore 56, and is of the same internal diameter for slidably receiving rod 54. For purposes of the continuing discussion, loading rod 54 includes a first longitudinal end 58 and a second longitudinal end 60. Loading rod first longitudinal end 58 has a diameter which is less than the external diameter of body member 36, and is typically and most preferably one-half or less than the size of the external diameter of body 36.

A force-sensitive transducer 62 is slidably received within body 26 and is positioned to engage relative to loading rod second longitudinal end 60. More particularly, transducer is slidably received within main body longitudinal cavity 44. Such is provided with opposing guide pins 64 which are slidably received in main body opposing slots 48. The force-sensitive transducer utilized in reduction-to-practice experiments was purchased from the Eaton Corporation of Troy, Mich.

Plug 38 is threadedly received within second threaded longitudinal opening 42 in main body 34. Plug 38 also includes an internal longitudinal threaded opening 66. A loading bolt 68 is threadedly received within threaded opening 66. Thus, loading bolt 68 is threadedly received relative to body 26. Loading bolt 68 has a bearing end surface 70 which extends outwardly of threaded plug 38 such that bolt 68 is positioned to ultimately bear against transducer 62 to forcibly sandwich transducer 62 between loading bolt 68 and loading rod 54. A force transfer plate 72 is slidably positioned within body 26 between loading bolt 68 and transducer 62. Force transfer plate 72 has opposing pins 74 which are slidably received within main body 34 longitudinal side slots 48. Force transfer plate 72 eliminates transfer of torsional forces from loading bolt 48 to force transducer 62. Threaded bolt end surface 70 is radiused, thereby reducing contact area between bolt 68 and transducer 62 through transfer plate 72, as compared to a flat bearing end surface for bolt 68. Plug 38 enables easy installation of the force transducer and transfer plate into the main body.

Operation and example methods of use in accordance with the invention are now described with reference to FIG. 6. Threaded extension 32/36 is fully threaded into threaded opening 14 of specimen sample 10 to cause reference bearing surface 50 of main body 34 to bear against the external portion of the test specimen. This will position the outer end of longitudinal extension 36 within notch 12, but displaced from bearing against load surface 20 of tup 18. Alternate constructions are of course possible, with the invention only being limited by the accompanying claims appropriately interpreted in accordance with the Doctrine Of Equivalents. For example, the length of adapter 36 might be such that its outermost end does not extend into notch 12. Regardless, bolt 68 is threaded inwardly to bring each of transfer plate 72, transducer 62, and loading rod 54 into contacting relation, with first end 58 of loading rod 54 bearing against loading surface 20 of load tup 18. Thereafter, bolt 68 is continued to be threaded inwardly to test specimen 10 to apply a predetermined force or desired notch mouth opening displacement to specimen 10. Applied force on test specimen 10 is determined as a function of time from readings obtained from force-sensitive transducer 62.

Such a method and apparatus has significant improvements over those of the prior art referred to above. For example, longitudinal end 58 of loading rod 54 is considerably smaller in longitudinal cross-section than the end of prior art load bolts 22 (FIG. 1). Additionally, first longitudinal end 58 does not rotate against tup 18. Relative rotation does occur between loading bolt end bearing surface 70 and loading plate 72, but torsional force is minimized due to the radiused end of loading bolt 68. Further, such end radius minimizes torque against loading plate 72 which might otherwise undesirably cause undue stress against shear pins 74 and 64. Such system further enables measurement of all load occurring before, during and at the end of the testing sequence.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A bolt-loaded compact tension test specimen load apparatus, the specimen having a notch and a threaded opening extending to and positioned transversely relative to the notch for receiving a threaded bolt for applying an opening force to the notch, the load apparatus comprising:

a body having first and second opposing longitudinal ends, the first end comprising an externally threaded portion sized to be threadedly received within the test specimen threaded opening;

a longitudinal loading rod having first and second opposing longitudinal ends, the loading rod being slidably received in a longitudinal direction within the body internally through the externally threaded portion and slidably extending longitudinally outward of the body first longitudinal end;

a force sensitive transducer slidably received within the body and positioned to engage relative to the loading rod second longitudinal end; and a loading bolt threadedly received relative to the body, the loading bolt having a bearing end surface and being positioned to bear against the transducer to forcibly sandwich the transducer between the loading bolt bearing end and second end of the loading rod.

2. The load apparatus of claim 1 wherein the body externally threaded portion has a minor thread diameter, the loading rod first longitudinal end having a diameter which is less than the minor thread diameter.

3. The load apparatus of claim 1 wherein the body externally threaded portion has a minor thread diameter, the loading rod first longitudinal end having a diameter which is one-half or less than the minor thread diameter.

4. The load apparatus of claim 1 wherein the bearing end of the loading bolt is radiused, thereby reducing contact area between the bolt and transducer as compared to a flat bearing end.

5. The load apparatus of claim 1 wherein, the test specimen notch has an open notch spacing and the specimen threaded opening has a length from the exterior of the specimen to the notch, the spacing and length having a sum defining a first distance; and the body comprises a main body portion and the externally threaded portion comprises a longitudinal extension extending from the main body portion, the main body comprising a bearing surface adjacent the longitudinal extension, the longitudinal extension extending longitudinally from the main body bearing surface to a second distance, the second distance being effectively less than the first distance to enable contacting of the main body bearing surface against the exterior of the test specimen when the longitudinal extension is fully threaded inwardly relative to the test specimen threaded opening.

6. The load apparatus of claim 5 wherein the bearing surface is formed on an annular ring which encircles the longitudinal extension.

7. The load apparatus of claim 1 wherein, the body comprises a main body portion having a first longitudinal threaded opening at the first end, the main body first threaded opening being of the same diameter as the test specimen threaded opening; and the externally threaded portion comprises a discrete longitudinally elongated body which is threadedly received within the main body first threaded opening.

8. The load apparatus of claim 1 wherein, the test specimen notch has an open notch spacing and the specimen threaded opening has a length from the exterior of the specimen to the notch, the spacing and length having a sum defining a first distance;

the body comprises a main body portion having a first longitudinal threaded opening at the first end and an adjacent lateral bearing surface, the main body first threaded opening being of the same diameter as the test specimen threaded opening; and the externally threaded portion comprises a discrete longitudinally elongated body which is threadedly received within the main body first threaded opening, the discrete body extending longitudinally from the main body bearing surface to a second distance, the second distance being effectively less than the first distance to enable contacting of the main body bearing surface against the exterior of the test specimen when the longitudinal extension is fully threaded inwardly relative to the test specimen threaded opening.

9. A bolt-loaded compact tension test specimen load apparatus, the specimen having a notch and a threaded opening extending to and positioned transversely relative to the notch for receiving a threaded bolt for applying an opening force to the notch, the load apparatus comprising:

a body having first and second opposing longitudinal ends, the first end comprising an externally threaded portion sized to be threadedly received within the test specimen threaded opening;

a longitudinal loading rod having first and second opposing longitudinal ends, the loading rod being slidably received in a longitudinal direction within the body internally through the externally threaded portion and slidably extending longitudinally outward of the body first longitudinal end;

a force sensitive transducer slidably received within the body and positioned to engage relative to the loading rod second longitudinal end;

a force transfer plate slidably positioned within the body between the loading bolt and the transducer; and a loading bolt threadedly received relative to the body, the loading bolt having a bearing end surface and being positioned to bear against the transducer to forcibly sandwich the transducer between the loading bolt and loading rod.

10. The load apparatus of claim 1 wherein the body comprises a longitudinal threaded opening, the apparatus further comprising an externally threaded plug threadedly received within the body longitudinal threaded opening, the plug having internal threads sized to receive the loading bolt, the loading bolt being longitudinally threaded into the plug with the loading bolt bearing end surface extending out of the plug.

11. The load apparatus of claim 9 wherein the bearing end of the loading bolt is radiused, thereby reducing contact area between the bolt and transducer as compared to a flat bearing end.

12. The load apparatus of claim 9 wherein, the body externally threaded portion has a minor thread diameter, the loading rod first longitudinal end having a diameter which is less than the minor thread diameter; and the bearing end of the loading bolt is radiused, thereby reducing contact area between the bolt and transducer as compared to a flat bearing end.

13. The load apparatus of claim 9 wherein, the body externally threaded portion has a minor thread diameter, the loading rod first longitudinal end having a diameter which is one-half or less than the minor thread diameter; and the bearing end of the loading bolt is radiused, thereby reducing contact area between the bolt and transducer as compared to a flat bearing end.

14. The load apparatus of claim 9 wherein, the body externally threaded portion has a minor thread diameter, the loading rod first longitudinal end having a diameter which is one-half or less than the minor thread diameter;

the bearing end of the loading bolt is radiused, thereby reducing contact area between the bolt and transducer as compared to a flat bearing end; and the body comprises a longitudinal threaded opening, the apparatus further comprising an externally threaded plug threadedly received within the body longitudinal threaded opening, the plug having internal threads sized to receive the loading bolt, the loading bolt being longitudinally threaded into the plug with the loading bolt bearing end surface extending out of the plug.

15. The load apparatus of claim 9 wherein, the test specimen notch has an open notch spacing and the specimen threaded opening has a length from the exterior of the specimen to the notch, the spacing and length having a sum defining a first distance;

the bearing end of the loading bolt is radiused, thereby reducing contact area between the bolt and transducer as compared to a flat bearing end; and the body comprises a main body portion and the externally threaded portion comprises a longitudinal extension extending from the main body portion, the main body comprising a bearing surface adjacent the longitudinal extension, the longitudinal extension extending longitudinally from the main body bearing surface to a second distance, the second distance being effectively less than the first distance to enable contacting of the main body bearing surface against the exterior of the test specimen when the longitudinal extension is fully threaded inwardly relative to the test specimen threaded opening.

16. The load apparatus of claim 15 wherein the bearing surface is formed on an annular ring which encircles the longitudinal extension.

17. The load apparatus of claim 9 wherein, the test specimen notch has an open notch spacing and the specimen threaded opening has a length from the exterior of the specimen to the notch, the spacing and length having a sum defining a first distance;

the bearing end of the loading bolt is radiused, thereby reducing contact area between the bolt and transducer as compared to a flat bearing end;

the body comprises a main body portion having a first longitudinal threaded opening at the first end, the main body first threaded opening being of the same diameter as the test specimen threaded opening; and the externally threaded portion comprises a discrete longitudinally elongated body which is threadedly received within the main body first threaded opening.

18. The load apparatus of claim 9 wherein, the test specimen notch has an open notch spacing and the specimen threaded opening has a length from the exterior of the specimen to the notch, the spacing and length having a sum defining a first distance;

the bearing end of the loading bolt is radiused, thereby reducing contact area between the bolt and transducer as compared to a flat bearing end;

the body comprises a main body portion having a first longitudinal threaded opening at the first end and an adjacent lateral bearing surface, the main body first threaded opening being of the same diameter as the test specimen threaded opening;

the externally threaded portion comprises a discrete longitudinally elongated body which is threadedly received within the main body first threaded opening, the discrete body extending longitudinally from the main body bearing surface to a second distance, the second distance being effectively less than the first distance to enable contacting of the main body bearing surface against the exterior of the test specimen when the longitudinal extension is fully threaded inwardly relative to the test specimen threaded opening; and the load apparatus further comprising a force transfer plate slidably positioned within the body between the loading bolt and the transducer.

19. A method of in situ determination of applied force during crack propagation in a bolt-loaded compact tension test specimen, the method comprising the following steps:

providing a rod in a transversely slidable orientation relative to a notch in a bolt-loaded compact tension test specimen, the rod having first and second opposing ends, the first end being positioned and adapted for bearing against one transverse surface of the test specimen exposed by the notch;

providing a force sensitive transducer operatively against the second end of the loading rod;

threading a bolt operatively against the transducer to force the first rod end against the one transverse surface of the test specimen to load the test specimen; and determining applied force on the test specimen as a function of time from readings obtained from the force sensitive transducer.

* * * * *